US009492171B2

(12) United States Patent
Patenaude (10) Patent No.: US 9,492,171 B2
(45) Date of Patent: Nov. 15, 2016

(54) ATRAUMATIC WOUND CARE AND CLOSURE SYSTEM (71) Applicant: Creative Technology Concepts LLC, Kansas City, MO (US)

(72) Inventor: Bart Patenaude, Kansas City, MO (US)

(73) Assignee: Creative Technology Concepts LLC, Kansas City, MO (US)

( * ) Notice: Subject to any disclaimer, the term of this patent is extended or adjusted under 35 U.S.C. 154(b) by 0 days.

(21) Appl. No.: 14/342,322

(22) PCT Filed: Jul. 24, 2013

(86) PCT No.: PCT/US2013/051878
§ 371 (c)(1),
(2) Date: Feb. 28, 2014

(87) PCT Pub. No.: WO2014/116302
PCT Pub. Date: Jul. 31, 2014

(65) Prior Publication Data
US 2015/0313593 A1 Nov. 5, 2015

Related U.S. Application Data (63) Continuation of application No. PCT/US2013/031502, filed on Mar. 14, 2013.
(Continued)

(51) Int. Cl.
*A61F 13/00* (2006.01)
*A61B 17/08* (2006.01)
(Continued)

(52) U.S. Cl.
CPC ......... *A61B 17/085* (2013.01); *A61B 17/0466* (2013.01); *A61F 13/00021* (2013.01);
(Continued)

(58) Field of Classification Search
CPC ............ A61F 13/49413; A61F 13/4942; A61F 13/15593; A61F 13/15723; A61F
(Continued)

(56) References Cited

U.S. PATENT DOCUMENTS 3,135,258 A * 6/1964 Billings .................. A61F 13/04
602/8
3,677,250 A 7/1972 Thomas
(Continued)

FOREIGN PATENT DOCUMENTS

EP 279701 2/2011
GB 321649 11/1929
(Continued)

OTHER PUBLICATIONS

International Preliminary Report on Patentability in Corresponding PCT/US2013/031502, mailed Aug. 6, 2015 (10 pages).
(Continued)

*Primary Examiner* — Michael Brown
(74) *Attorney, Agent, or Firm* — Hovey Williams LLP (57) ABSTRACT An article useful for atraumatic care and/or closure of wounds, as well as for repairing torn or ripped fabric is provided. The article comprises a substrate having opposing first and second major surfaces, a plurality of raised anchoring members disposed across the first major surface, and an optional adhesive pre-mounted adjacent the second major surface. A separate adhesive could also be used to mount the article to the desired underlying surface to be repaired. The substrate is a flexible and conformal continuous web that can be cut into pieces to custom fit the wound or fabric opening. Using the anchoring members and a thread, the pieces can be drawn together to correspondingly draw the tissue or fabric on either side(s) of the opening together, thereby closing the opening without piercing or suturing/sewing
(Continued)

together the underlying tissue or fabric. Methods for the atraumatic care and/or closure of wounds, as well as for repairing torn or ripped fabric are also provided, including kits to facilitate the same.

20 Claims, 9 Drawing Sheets

Related U.S. Application Data (60) Provisional application No. 61/756,931, filed on Jan. 25, 2013.

(51) Int. Cl.
*A61M 16/00* (2006.01)
*A61M 25/02* (2006.01)
*A61M 16/04* (2006.01)
*A61B 17/04* (2006.01)

(52) U.S. Cl.
CPC ..... *A61M 16/0003* (2014.02); *A61M 16/0465* (2013.01); *A61M 25/02* (2013.01); *A61B 2017/081* (2013.01); *A61B 2017/086* (2013.01); *A61M 2025/024* (2013.01); *A61M 2025/0266* (2013.01); *Y10T 428/24017* (2015.01)

(58) Field of Classification Search
CPC .................. 13/15747;A61F 13/15756; A61F 13/42; A61F 13/49001; A61F 13/49406; A61F 13/532; A61F 13/5323; A61F 2013/422; A61F 13/0203; A61F 13/023; A61F 13/02; A61F 13/0273; A61F 13/0276; A61F 13/08; A61F 15/001; A61F 2013/00123; A61F 2013/0028; A61F 2013/008; A61F 13/00068; A61F 2013/00174; A61F 2013/00536; A61F 13/0216; A61F 13/00085; A61F 13/105; A61F 15/02; A61B 17/00491; A61B 17/085; A61B 17/083; A61B 2017/00867; A61L 15/58; A61L 15/60; A61L 15/425; A44B 18/0049; A44B 18/0057; A44B 18/0061; A44B 18/0073; A44B 18/0088; A44B 17/00491; A44B 17/085; A44B 5/04087; A61M 1/0058; A61M 1/006
USPC ...................................... 602/41–54
See application file for complete search history.

(56) References Cited

U.S. PATENT DOCUMENTS

| | | | |
|---|---|---|---|
| 3,934,592 A | 1/1976 | Wolvek et al. |
| 4,526,173 A | 7/1985 | Sheehan |
| 4,815,468 A | 3/1989 | Annand |
| 4,825,866 A | 5/1989 | Pierce |
| 4,897,082 A | 1/1990 | Erskine |
| 4,962,757 A | 10/1990 | Stefan |
| 5,176,703 A | 1/1993 | Peterson |
| 5,234,462 A | 8/1993 | Pavletic |
| 5,263,970 A | 11/1993 | Preller |
| D371,604 S | 7/1996 | Savage et al. |
| 5,545,123 A | 8/1996 | Ortiz et al. |
| 5,665,108 A | 9/1997 | Galindo |
| 6,007,564 A | 12/1999 | Haverstock |
| 6,106,544 A | 8/2000 | Brazeau |
| 6,176,868 B1 | 1/2001 | Detour |
| D457,241 S | 5/2002 | Dunshee et al. |
| D457,629 S | 5/2002 | Dunshee et al. |
| D458,371 S | 6/2002 | Dunshee et al. |
| D461,007 S | 7/2002 | Dunshee et al. |
| D465,572 S | 11/2002 | Dunshee et al. |
| 6,595,938 B1* | 7/2003 | Delmore ................. A61F 13/04 602/1 |
| 6,712,839 B1 | 3/2004 | Lonne |
| D492,411 S | 6/2004 | Bierman |
| 6,752,794 B2* | 6/2004 | Lockwood .......... A61M 1/0058 604/313 |
| 7,066,182 B1 | 6/2006 | Dunshee |
| 7,267,681 B2 | 9/2007 | Dunshee |
| 7,354,446 B2 | 4/2008 | Lebner |
| 7,361,185 B2 | 4/2008 | O'Malley et al. |
| 7,429,265 B2 | 9/2008 | O'Malley et al. |
| 7,511,185 B2 | 3/2009 | Lebner |
| 7,547,315 B2 | 6/2009 | Peterson et al. |
| 7,686,829 B2 | 3/2010 | Elliott et al. |
| 7,696,399 B2 | 4/2010 | Rogers |
| 7,834,232 B2 | 11/2010 | Rastegar et al. |
| 7,838,718 B2 | 11/2010 | Lebner |
| 7,981,136 B2 | 7/2011 | Weiser |
| 8,066,735 B2 | 11/2011 | Warren |
| 8,105,353 B2 | 1/2012 | Lebner et al. |
| 8,157,839 B2 | 4/2012 | Riskin et al. |
| 8,518,077 B2 | 8/2013 | O'Malley et al. |
| 2003/0069531 A1* | 4/2003 | Hall ..................... A61F 5/01 602/75 |
| 2007/0088339 A1 | 4/2007 | Luchetti |
| 2008/0114396 A1 | 5/2008 | Cory et al. |
| 2008/0228220 A1 | 9/2008 | Weiser |
| 2008/0262524 A1 | 10/2008 | Bangera et al. |

FOREIGN PATENT DOCUMENTS

| | | |
|---|---|---|
| GB | 2364246 | 1/2002 |
| RU | 2259172 C2 | 2/2005 |
| WO | 93/08748 A1 | 5/1993 |
| WO | 96/10954 A1 | 4/1996 |
| WO | 2004/006782 A1 | 1/2004 |
| WO | 2005/002452 A1 | 1/2005 |
| WO | 2005/009276 A2 | 2/2005 |
| WO | 2009/123893 A1 | 10/2009 |

OTHER PUBLICATIONS

International Preliminary Report on Patentability in Corresponding PCT/US2013/051878, mailed Aug. 6, 2015 (5 pages).
International Search Report and Written Opinion of the International Searching Authority in related application PCT/US2013/031502 mailed Oct. 8, 2013 (15 pages).
International Search Report and Written Opinion of the International Searching Authority in related application PCT/US2013/051878 mailed Dec. 5, 2013 (8 pages).
Czech et al, "Pressure-Sensitive Adhesives for Medical Applications", ISBN: 978-953-307-683-6, InTech, Jul. 2011 (25 pages).
"Protecting Skin with Low Trauma Adhesives", FABRICO, a division of EIS, www.fabrico.com, printed Feb. 2013 (2 pages).
"Wound Closure Manual", Ethicon, Inc., a Johnson-Johnson company, 2005 (127 pages).
MediGROUP Australia—Products "ABRA Adhesive Skin Closure for Retracted Skin Defects", www.medigroup.com.au/adhesiveskinclosure, Oct. 30, 2013 (6 pages).
"Canica Design Awarded Milestone U.S. Patent for Dynamic Wound Closure Systems", Canica press release dated Jul. 29, 2008 (2 pages).
Canica ABRA Adhesive Skin Closure Set Instructions for Use, Canica Designs, Inc., Nov. 12, 2009 (2 pages).
ABRA Adhesive Skin Closure, www.pro-motionmedical.eu/products/abra-adhesive-skin-closure.html, Oct. 24, 2013 (2 pages).
womenpretty.ru, Kak postavit nezametnuyu zaplatu. Shiem sami, Nov. 21, 2011, pp. 1-4 (retrieved on Sep. 16, 2013), retrieved from the internet http://www.womenpretty.ru/zaplata.html (4 pages).

(56) References Cited

OTHER PUBLICATIONS

International Supplementary European Search Report on Patentability in Corresponding PCT/US2013/051878, mailed Aug. 18, 2016 (11 pages).

* cited by examiner

ATRAUMATIC WOUND CARE AND CLOSURE SYSTEM

CROSS-REFERENCE TO RELATED APPLICATIONS

The present application is the National Stage of PCT/US2013/051878, filed Jul. 24, 2013, which claims the priority benefit of PCT/US2013/031502, filed Mar. 14, 2013, and U.S. Provisional Patent Application Ser. No. 61/756,931, filed Jan. 25, 2013, each entitled ATRAUMATIC WOUND CARE AND CLOSURE SYSTEM, and incorporated by reference in its entirety herein.

BACKGROUND

1. Field of the Invention

The present disclosure relates to an article, system, and method for the closure of wounds, tears, and rips, without piercing the underlying torn tissue or fabric.

2. Description of Related Art

Traditional wound closure techniques involve the use of sutures, commonly known as stitches, while more modern techniques utilize staples, adhesives, hemostats, and/or sealants. The primary function of a wound closure device or technique is to close a wound, both internal and external, and stop the bleeding through hemostasis. And important secondary function that wound closure techniques are expected to perform is avoiding or minimizing scarring. Scarring is particularly relevant with respect to facial wounds, as well as in cosmetic surgery procedures. Another problem posed by tissue wounds is the fact that many wounds are not straight cuts on a flat surface. Rather, living bodies are curved and contoured, and wounds are typically irregular. For example, stellate lacerations contain several V-shaped openings, wherein the tip of the V has already been compromised. Using a suture or staple through that tissue will only further compromise the tissue and the blood supply. Thus, even current wound closure techniques suffer drawbacks and there remains a need in the art for wound closure techniques that avoid further traumatization to the wound tissue.

SUMMARY

The present disclosure is broadly concerned with an article for the atraumatic closure of a wound, atraumatic securement of medical devices, and/or general atraumatic wound care. The article is also useful for the closure of ripped or torn fabric. The article is particularly useful for the treatment, care, and/or closure of open wounds, such as abrasions, burns, incisions, lacerations/tears, punctures, avulsions, and the like. In general, the article comprises a substrate having opposing first and second major surfaces, a plurality of raised thread-receiving or thread-securing anchoring members disposed across the first major surface, and an optional adhesive adjacent (i.e., face-to-face contact with) the second major surface. The adhesive is operable for securing the article to the tissue or fabric to be repaired and can be provided already mounted to the article. Alternatively, the adhesive can be separately provided and first applied to the tissue or fabric, followed by securing the article to the tissue or fabric with the second major surface adjacent (i.e., face-to-face contact with) the adhesive.

A system for atraumatic wound care and/or closure is also provided. The system comprises an article useful for atraumatic closure of a wound, as described herein, and a thread.

A method for the atraumatic closure of a tissue wound of a subject is also disclosed. The wound has wound edges, and the method generally comprises providing an article useful for atraumatic closure of a wound, as described herein, and a thread. The article substrate is adhered to the subject's tissue adjacent (i.e., next to) the wound edges on a first side of the wound and a second side of the wound opposite the first side. The wound edges are then reapproximated. Wound reapproximation is carried out by realigning the disrupted tissue planes by securing the thread to a first anchoring member on the first side of the wound, passing the thread to the second side of the wound opposite the first side and securing the thread to a second anchoring member. This process is repeated along the edges of the wound keeping the thread under tension to pull the tissue from the first side of the wound towards the tissue on the second side of the wound thereby ultimately closing the wound.

The present disclosure is also concerned with a kit for the atraumatic closure of a wound. The kit comprises an article useful for atraumatic closure of a wound, as described herein, and optionally a thread, and adhesive, along with instructions for using the article and a thread to close a wound A method for the atraumatic care of a wound of a subject is also disclosed herein. The wound has wound edges, and the method generally comprises providing an article useful for atraumatic care of a wound, as described herein, and a thread. The article substrate is adhered to the subject's tissue adjacent (i.e., next to) the wound edges on a first side of the wound and a second side of the wound opposite the first side. The wound (which can optionally be packed and/or covered with a skin graft) is covered with a dressing. The dressing is then secured to the wound by securing the thread to a first anchoring member on the first side of the wound, passing the thread over the dressing to the second side of the wound opposite the first side and securing the thread to a second anchoring member. This process is repeated along the wound edges keeping the thread under sufficient tension to press the dressing towards the wound and frictionally secure it to the wound. Alternatively, the thread can be passed through the dressing for additional stability and securement.

The present disclosure is also concerned with a method for the atraumatic securement of a medical device to a patient's tissue using the inventive system. The method generally comprises providing an article useful for atraumatic care of a wound, as described herein, and a thread. A medical device is inserted into the patient. The article substrate is adhered to the patient's tissue adjacent (i.e., next to) where the device has been inserted into the patient on a first side of the device and on a second side of the device opposite the first side. A thread is secured to a first anchoring member on the first side of the device and also to the device itself. A thread (same or different) is also secured to a second anchoring member on the second side of the device and to the device itself. The thread on each side of the device is under opposing forces (tension), which stabilizes the device and prevents dislodgement of the device from the patient.

A method of repairing torn or ripped fabric on a stuffed toy is also disclosed herein. The toy comprises an opening in the fabric corresponding to a tear or rip, and has opening edges. The method comprises providing an article useful for repairing torn or ripped fabric, as described herein, and a thread. The article substrate is adhered to the fabric adjacent (i.e., next to) the edges on a first side of the tear or rip and a second side of the tear or rip opposite the first side. The opening edges are brought together by securing the thread to a first anchoring member on the first side of the tear or rip, passing the thread to the second side of the tear or rip opposite the first side and securing the thread to a second anchoring member. This process is repeated along the opening edges, keeping the thread under tension to pull the fabric from the first side of the tear or rip towards the fabric on the second side of the tear or rip thereby closing the opening and repairing the torn or ripped fabric.

A kit for repairing torn or ripped fabric on a stuffed toy is also described herein. The kit comprises an article useful for repairing torn or ripped fabric, as described herein, and optionally a thread and adhesive, along with instructions for using the article and a thread to close the opening and repair the fabric.

BRIEF DESCRIPTION OF THE DRAWINGS

Figure (FIG. 1 is a perspective view of one embodiment of the atraumatic wound care and/or closure system, including thread.

DETAILED DESCRIPTION OF PREFERRED EMBODIMENTS

Figure 1:
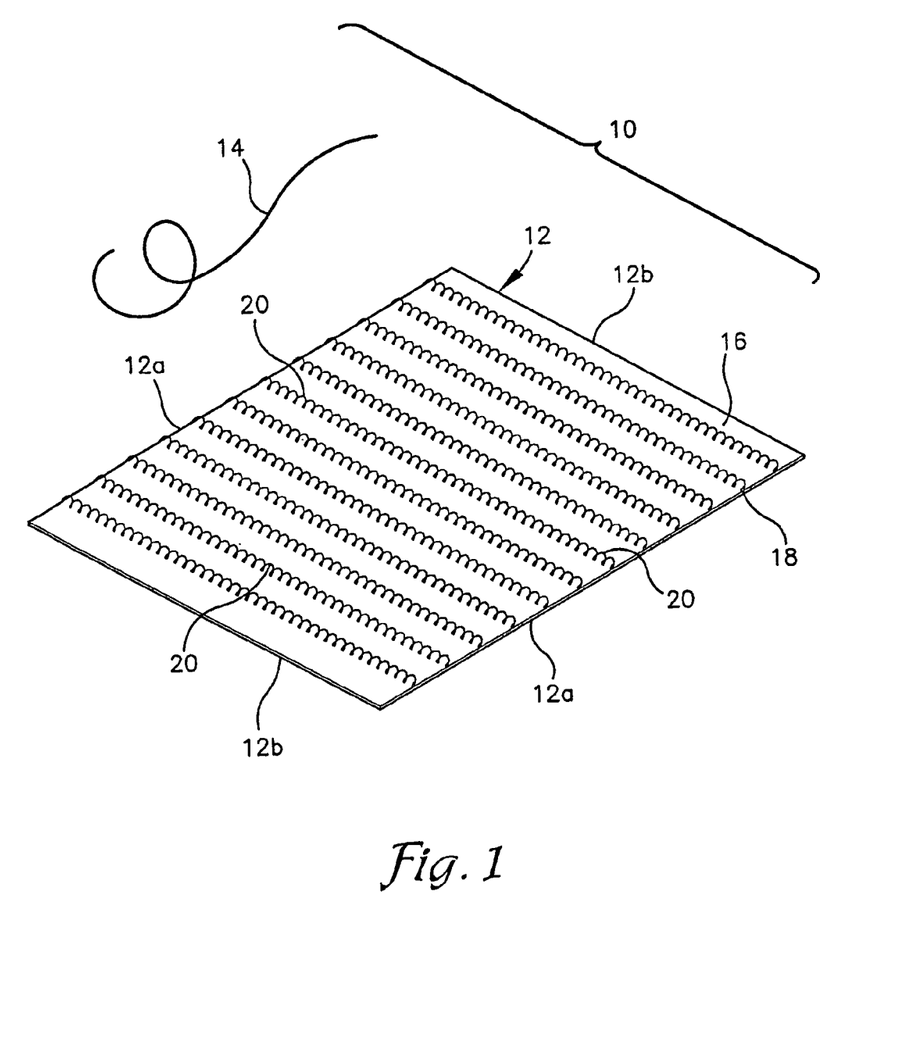

The present disclosure is concerned with a wound care and/or closure system for atraumatic care and/or closure of wounds. The term "atraumatic" is used herein to denote that the wound care and/or closure system involves no penetration or piercing of the subject's tissue, for example with a needle, staples, or other conventional suturing or wound closure techniques. With reference to FIG. 1, the wound care and/or closure system 10 comprises an article substrate 12 and optionally a thread 14. The substrate 12 comprises first and second opposing major surfaces, referred to herein as a front surface 16 and a back surface 18, respectively. The substrate 12 comprises a continuous web or sheet that is flexible in all directions and conformal to underlying surfaces to which the substrate 12 may be applied, such as for example, conformable topical application to human or animal skin. The substrate 12 can be provided in various shapes and sizes, including an elongated sheet, rectangular, circular, triangular, or other shape. For example, the substrate 14 can have a pair of laterally-spaced longitudinal side edges 12a and a pair of laterally spaced transverse ends 12b, defining a substantially rectangular or square shape, as depicted in FIG. 1. In other embodiments, the substrate 12 can have an annular lateral edge defining a substantially circular shape or three lateral edges forming a triangular shape (not shown).

The substrate 12 may be a woven or nonwoven web (also referred to in the medical tape art as a backing), and may be composed of natural, synthetic, or a combination thereof of fibers. Examples of natural fibers include cotton, silk, hemp, flax, and the like. Examples of synthetic fibers include rayon, polyester, acrylic, acrylate, polyolefin, nylon, polyurethane, polyethylene, polypropylene, polyamide, polytetrafluoroethylene, wire mesh, embedded wire clothe (e.g., butterfly tape), and the like. The substrate 12 may also be a laminated or extruded sheet. Foam substrates 12 may also be used. In some embodiments, the substrate materials are preferably biocompatible. In some embodiments, the substrate comprises a woven or nonwoven breathable material. In one or more embodiments, the substrate is preferably substantially free of metals or other rigid materials. It will be appreciated that materials conventionally useful as backing for medical tapes and dressings are particularly suitable for use as the substrate material. Some exemplary tapes include those available from 3M: Kind Removal Silicon Tape, Medipore Cloth Tape, Transpore White Tape, Micropore, Durapore, Blenderm, and the like. In some embodiments, the web itself may be comprised of multiple layers (i.e., multilayered). The average thickness of the substrate 12 will generally range from about 1 mil (0.001 inch) to about 10 mil (0.010 inch), preferably from about 1 mil to about 5 mil, and more preferably from about 2 mil to about 5 mil. The thickness of the substrate 12 preferably has little variation across the expanse of the substrate. In other words, the thickness of the substrate is preferably substantially uniform as measured between the first and second major surfaces edge-to-edge. A significant advantage of the inventive substrate is that it is severable 12. As used herein, the term "severable" means that the substrate 12 can be cross-sectionally torn or cut into one or more pieces that conform to the shape of the wound opening to be closed. In other words, the term is directed towards cutting through the substrate 12 along a plane that cuts across (and is preferably generally perpendicular to) the plane defined by the front and back surfaces, and does not encompass separating the substrate along the plane defined by the front and back surfaces (for example, pulling apart layers in a multilayered substrate).

The front surface 16 of the substrate 12 comprises a plurality of raised anchoring members 20. The anchoring members 20 are disposed across the surface 16 and generally project away from the front surface 16 such that they are adapted to receive and secure (i.e., anchor) a thread 14 when the system 10 is in use (i.e., when the thread 14 is looped around or threaded through the anchoring members 20). In general, the anchoring members 20 will have respective heights, as measured from the front surface 16 of from about 1 mm to about 20 mm, preferably from about 2 mm to about 10 mm, and more preferably from about 2 mm to about 5 mm. Exemplary anchoring members include generally upright loops or half-loops, eyelets, raised or pleated mesh, hooks, pegs, prongs, nubs, generally upright strands of fiber (e.g., yarn), prone strands of fiber (e.g., yarn), generally upright pleats, or other protrusions that are comprised either of penetrable materials (e.g., rubber, plastic, composite, etc.) or configured to be looped around. For example, in some embodiments, the protrusions have a head and a throat around which the thread is wrapped whereby the head prevents the thread from disengaging the protrusion. The head may be angled to improve anchoring. In other embodiments, the protrusions are penetrable and adapted for passing the thread 14 through the protrusion itself (in one side and out the other), thereby anchoring the thread 14 to the front surface 16. In yet other embodiments, the anchoring member is an aperture, such as a loop, mesh opening, or eyelet, through which the thread 14 can be guided. Loops or half-loops can be formed by securing an elongated cord (or individual cord pieces) to the front surface 16 at various intervals across the surface to create a plurality of loops or half-loops as depicted in FIG. 1. The anchoring members 20 are each attached or secured to the substrate as appropriate for the particular anchoring member. For example, the anchoring members 20 can be sewn to or through the substrate, glued, tied, and the like. In some embodiments, the anchoring members 20 are integrally formed with the substrate 12. For example, the front surface 16 of the substrate 12 may be pleated, such that the pleats form anchoring members 20, which are formed of the same material as the substrate 12 itself (instead of being a separate piece that is subsequently attached thereto).

Particularly preferred anchoring member 20 configurations help distribute the pulling forces across the expanse of the substrate, such that the pulling force is not localized to any one area of tissue, as occurs with traditional suturing. In one or more embodiments, the anchoring members 20 will be disposed substantially uniformly across the front surface 16, for example as in a grid or matrix pattern. In other words, the density (number) of anchoring members 20 in a first portion of the front surface 16 will be substantially equivalent to the density of anchoring members 20 in a second, different portion of the front surface 16 having the same surface area. In one or more embodiments, the anchoring members 20 will be disposed in individual, separated groupings across the surface, which have spaces therebetween. In one or more embodiments, the anchoring members 20 will be randomly disposed across the surface 16.

Figure 6:
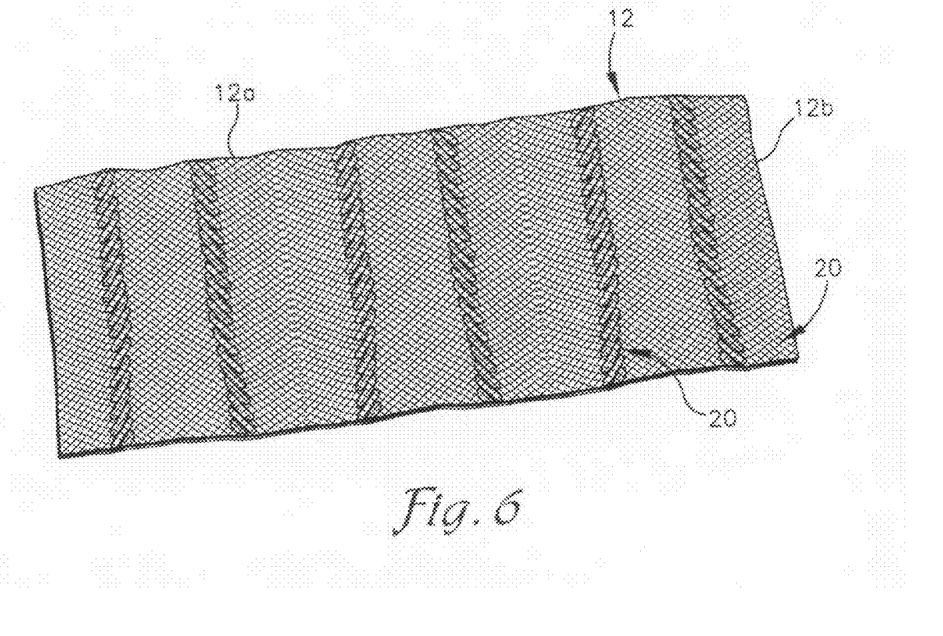
FIG. 6 illustrates a further embodiment of the wound care and/or closure article.

It will be appreciated that the front surface 16 can comprise the same type of anchoring member 20 across the surface. Alternatively, more than one type of the above-described anchoring members 20 can be used across the face of the front surface 16. Combinations of the above described materials can also be used to form the anchoring members 20. For example, a plurality of raised anchoring members (e.g., prone strands of yarn, nubs, etc.) can be covered with a substantially conformal layer of mesh. In use, the thread 14 can be guided through an opening in the mesh as well as through the corresponding raised anchoring member and out the other side through a corresponding opening in the mesh. Such an embodiment is depicted in FIG. 6.

The back surface 18 of the substrate 12 is configured to engage or contact an underlying surface, such as tissue or fabric to be repaired. The substrate 12 is attached to the underlying surface via an adhesive (aka glue) interposed between the back surface 18 of the substrate 12 and this underlying surface. In one or more embodiments, the adhesive is provided separately from the article 10. The adhesive is dispensed or applied onto the underlying surface, followed by mounting or attaching the article to the underlying surface with the back surface 18 of the substrate 12 adjacent (i.e., in face-to-face contact with) the adhesive. In one or more embodiments, the back surface 18 of the substrate 12 comprises an adhesive (or layer of adhesive) pre-mounted to the back surface 18, which can be in the form of a layer adjacent (i.e., in face-to-face contact with) the back surface 18. In one or more embodiments, the adhesive covers substantially the entire surface area of the back surface 18. In one or more embodiments, the peripheral margins of the back surface 18 remain substantially free of adhesive.

Regardless of the embodiment, suitable adhesives include pressure sensitive adhesives, as well as heat- or radiation-activated adhesives. It will be appreciated that the appropriate adhesive will depend upon the ultimate intended use of the system 10. For example, if the substrate 12 will be topically applied to skin, the adhesive should have good initial tack and long-term adhesion, and be able to tolerate the presence of moisture without releasing. Pressure-sensitive adhesives generally comprise elastomers that are inherently tacky or include tackifying resins. Exemplary adhesives for use in the invention include rubber elastomers, acrylics, acrylates (e.g., cyanoacrylates), epoxies, silicones, zinc oxides (or other hot melt adhesives), solvent-based adhesives, solvent-free adhesives, photosensitive adhesives, hydrocolloids, hydrogels, polyurethanes, styrene block co-polymers, and the like. In some embodiments, the adhesive is biocompatible. Numerous types of suitable adhesives are known in the art, and are commercially-available from suppliers such as 3M, Loctite (e.g., Duro-Tak), Adhesives Research, Ashland Chemical (e.g., Aroset), Dow (e.g., Robond), Polymer Science (e.g., Sofsil, Neosil), DuPont, and ITW Formex. Particularly preferred adhesives will have strong tissue adhesion properties, and adhesives suitable for use in medical tapes and dressings are preferred in some embodiments of the invention. For example, zinc oxide is currently considered a preferred adhesive for extreme adhesion needs. Low trauma adhesives can also be used.

The substrate 12 can be provided as one or more sheets or strips, each with a releasable liner covering the adhesive (when present) to prevent indiscriminate adherence or sticking of the substrate 12 to an undesired surface and/or preserve the adhesive properties of the adhesive layer and/or protect the adhesive layer from attracting dirt, debris, and the like until use. In some embodiments, the substrate 12 can be an elongated strip wound about a spool or dispensing apparatus. In one or more embodiments, the substrate 12 is provided as a large sheet that can be cut down to the necessary size. For example, dimensions such as 30 cm×30 cm are envisioned.

The thread (aka string, lace, cord, etc.) 14 can be any suitable type of elongated, woven or extruded threading material, such as cotton, nylon, polyester, polypropylene, silk, wire, stainless steel, plastic, cable (e.g., zip ties), and the like. Conventional suturing threads (2 mm or less, preferably 1 mm or less, more preferably 0.5 mm or less in diameter) are suitable for use with the invention (whether or not specifically provided for use with the system). The thread could be coated or uncoated. A needle (not shown) can be included for guiding the thread 14. A conventional metal needle may be used; however, since the system does not involve piercing the subject's skin, the needle may also be plastic or other suitably rigid material for guiding the thread 14 that is otherwise not sufficiently sharp or rigid to pierce skin tissue. Alternatively, the thread 14 itself can be provided with a substantially rigid end portion (at one or both ends) to facilitate feeding the thread through the anchoring members. The end portion of the thread can be made rigid by any suitable method, including the use of wax, resin, composite, glue, heat shrink, or melting the end portion of the thread. In some embodiments, the substantially rigid portion is a plastic or metal sheath (i.e., aglet) around the end portion of the thread. In some embodiments, the entire length of the thread is of sufficient rigidity to guide the thread through and/or around the anchoring members, such as in the case of wire or some plastic threads.

Figure 2A:
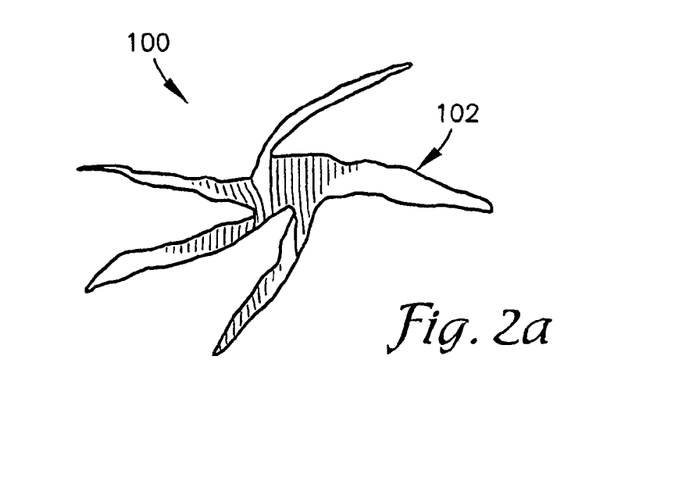
FIG. 2a is an illustration of a stellate laceration.
Figure 2B:
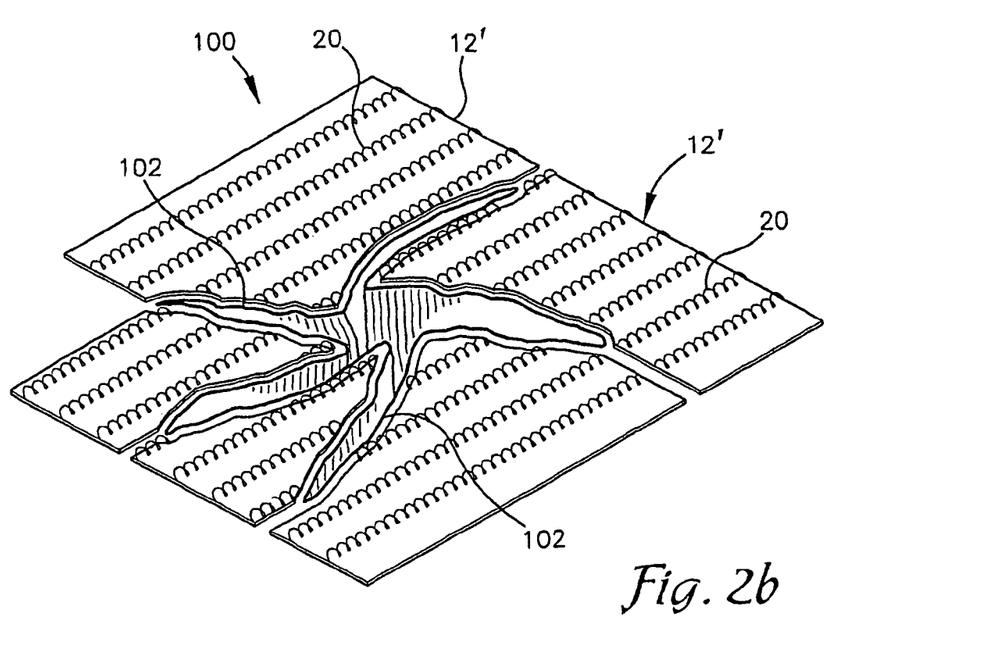
FIG. 2b is a perspective view of one embodiment of the atraumatic wound care and/or closure substrate article severed into pieces and adhered to tissue adjacent (i.e., next to) the stellate laceration edges.

The inventive substrate 12 is particularly advantageous for the atraumatic closure of wounds, as mentioned above. In one or more embodiments, a substrate 12 according to the invention is provided for use with a subject having a wound 100. The term wound is used herein to refer to injury or disruption to living tissue caused by a cut, blow, or other impact in which the skin is cut or broken, as well as to incisions (such as surgical incisions) into the skin. Thus, the term encompasses incisions, cuts, lacerations, burns, avulsions, necrosis, and the like of the skin (epidermis). Wounds can follow substantially straight lines, but are generally of irregular shape and contour depending upon the location of the body where the wound occurs. Stellate lacerations, which are illustrated in FIGS. 2a-2b, pose a particular problem for traditional suturing techniques. In one or more embodiments, a template can be used to determine the shape of the wound 12. For example, tissue paper or a like absorbent material (e.g., copy paper, cellulosic materials) can be pressed gently against the wound whereby the tissue paper absorbs fluid from the wound and provides an approximate shape for the wound. This shape is then transferred to the substrate 12. A particular advantage of the invention is that the substrate 12 can be cut (e.g., with scissors or a knife) to custom fit the wound 100. As shown in FIG. 2b, the severed pieces of the substrate 12 are then placed on (and adhered to) the skin of the subject, adjacent (i.e., next to and sharing a common border with) the wound edges 102, either using separately-applied adhesive or adhesive pre-mounted to the substrate 12. As noted above, the substrate 12 may first need to be released from the releasable liner to expose the adhesive layer, when pre-mounted onto the substrate. In some embodiments, to enhance adhesion, the tissue of the subject can be prepared before applying the substrate 12 or adhesive. Suitable skin preparation techniques include wiping the skin around and near the wound area with isopropyl alcohol (e.g., Preppies Skin Barrier Wipes; Kendall), betadine, chlorhexidine, and the like.

In some embodiments, the system 10 can further comprise an adhesive underlayment or intermediate layer (not shown) to which the substrate 12 is applied, instead of being applied directly to the tissue adjacent (i.e., next to) the wound. For example, an adhesive-backed substrate (e.g., medical tape) that includes a sufficiently strong adhesive for skin contact is applied to the subject. The substrate 12 is then applied to the adhesive-backed substrate to bond the substrate to the adhesive underlayment, rather than directly to the tissue of the subject. An example of this type of system is Rigid™ strapping tape, which is typically used for athletic immobilization.

Figure 3:
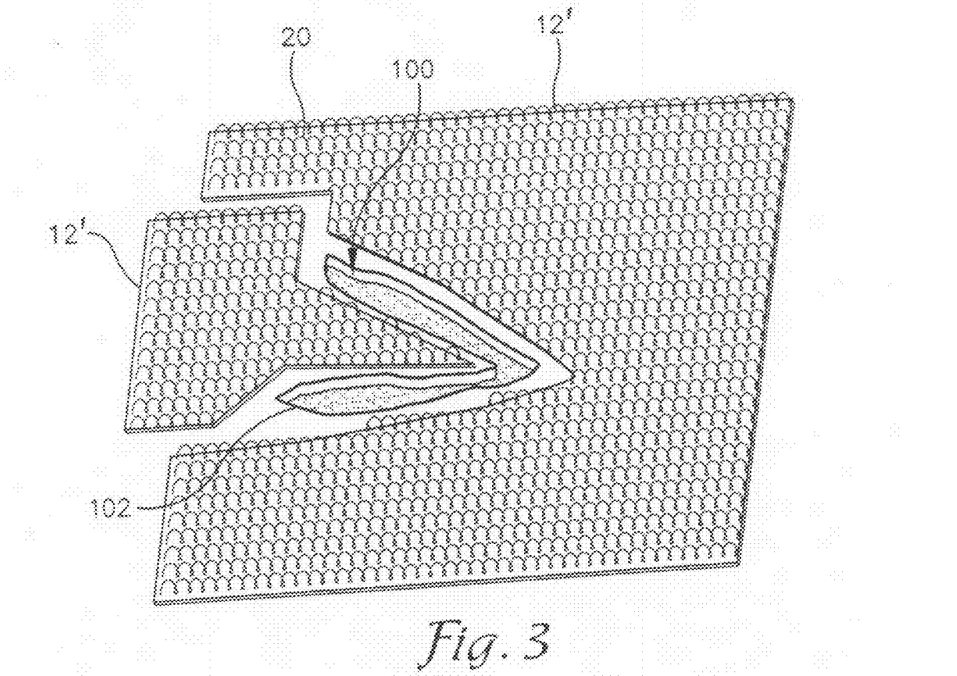
FIG. 3 is a further perspective view of one embodiment of the atraumatic wound care and/or closure substrate article severed into pieces and adhered to tissue adjacent (i.e., next to) the edges of a v-shaped wound.
Figure 4A:
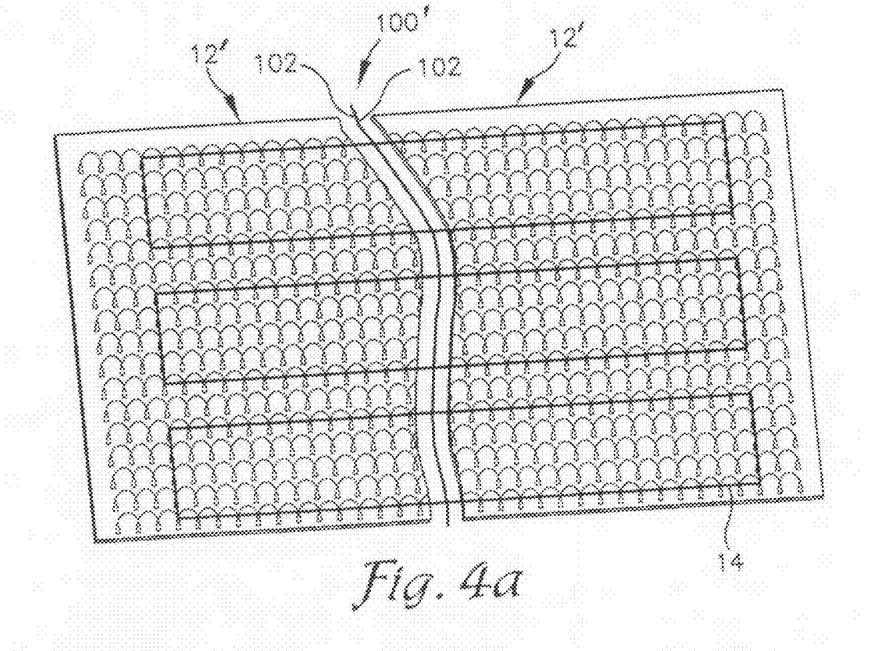
FIG. 4a is a top plan view of one embodiment of the atraumatic wound care and/or closure system and a wound closed by passing the thread back and forth across the wound to reapproximate the wound edges.
Figure 4B:
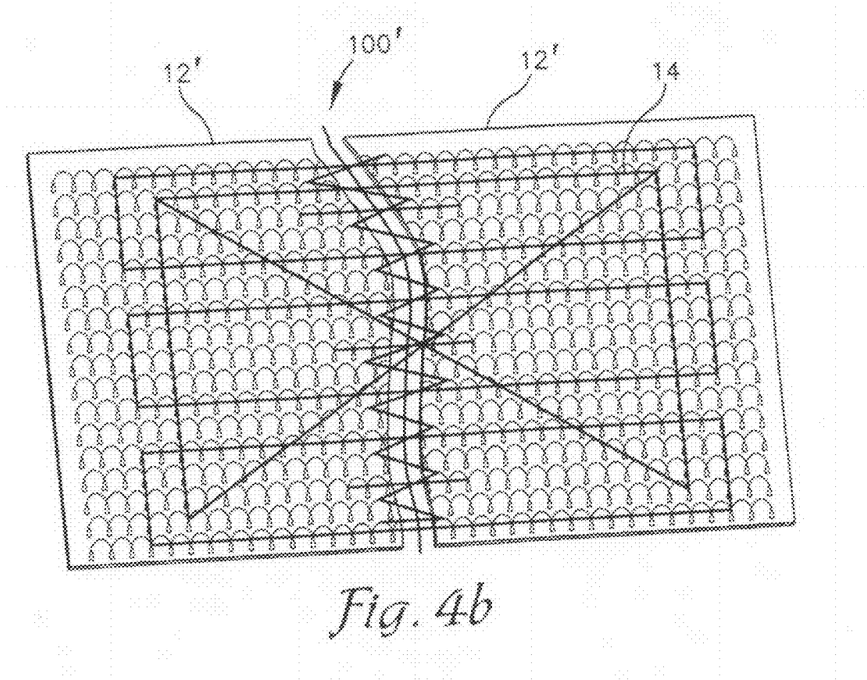
FIG. 4b is a top plan view of the system illustrating further threading to reinforce the system.

Regardless of the embodiment, once the piece or pieces of the substrate 12' are adhered to tissue adjacent (i.e., next to) to the wound edges 102, as depicted in FIG. 2b and FIG. 3, the inventive system 10 can be used to close the wound by re-approximating the wounded edges 102 together. More specifically, the thread 14 is secured to a first anchoring member 20 on one side of the wound (e.g., by tying it off on one of the anchoring members 20) and then passed to the other side of the wound where it is secured to/threaded through a second anchoring member 20 on the other side of the wound 100 such that tension is created on the side of the first anchoring member 20 pulling the tissue of the subject towards the second anchoring member 20. The back and forth process is repeated using various anchoring members 20 on either side of the wound edges 102 and thread 14 to keep tension on the tissue surrounding the wound 100, until the edges of the wound 102 are lined up and drawn or brought together, as depicted in FIG. 4a. Those skilled in the art will appreciate that one advantage of the invention is that instead of directly pulling the wound edges 102 together, the system 10 instead pulls the adjacent tissue, which in effect, pushes the wound edges 102 together. Thus, there is little to no additional localized trauma to the wound edges 102 in the present wound closure system 10. Additional lacing of the substrate can be performed as depicted in FIG. 4b to further support the tissue and the substrate, for example, to mitigate shearing forces on the wound 100. Those skilled in the art will recognize that the particular pattern of the sutureless method will depend to a certain extent on the shape and location of the wound. It will also be appreciated that the substrate pieces 12' can be "sutured" or laced together using a single continuous thread 14, or multiple threads 14 that are tied off at various points in the threading process. It will also be appreciated that the thread 14 can be passed through a single anchoring member 20 multiple times during the lacing process, which unlike a conventional suture, allows that single point to be tethered and stabilized from multiple directions, reducing any single directional force/tension on the tissue at that spot. This is particularly important, for example, in the tip of a v-shaped laceration which must be pulled in several different directions to re-approximate the tissue. With traditional suturing or staples, this small section of tissue is ordinarily fragile and prone to tearing and further trauma. Such trauma is avoided by the present invention.

Figure 5A:
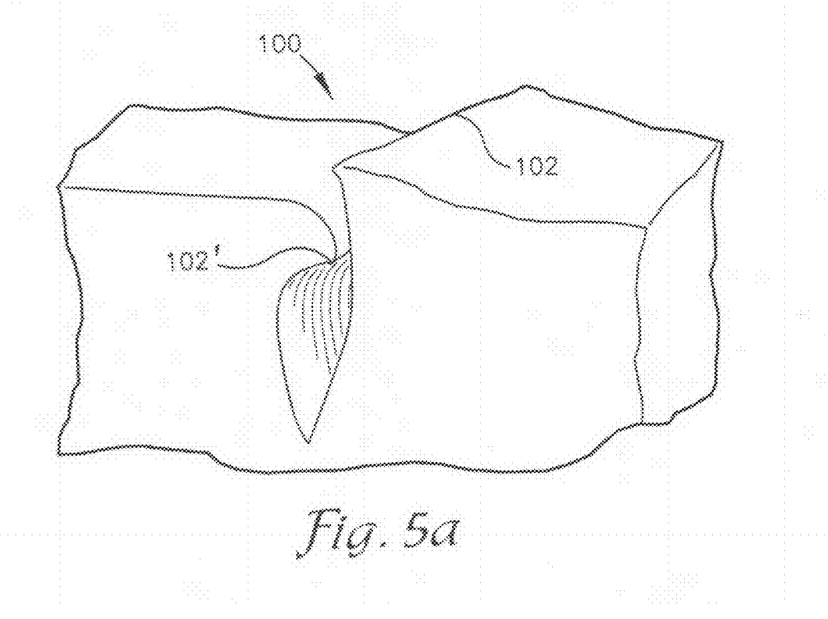
FIG. 5a is a cross-section illustration of an inverted wound edge.
Figure 5B:
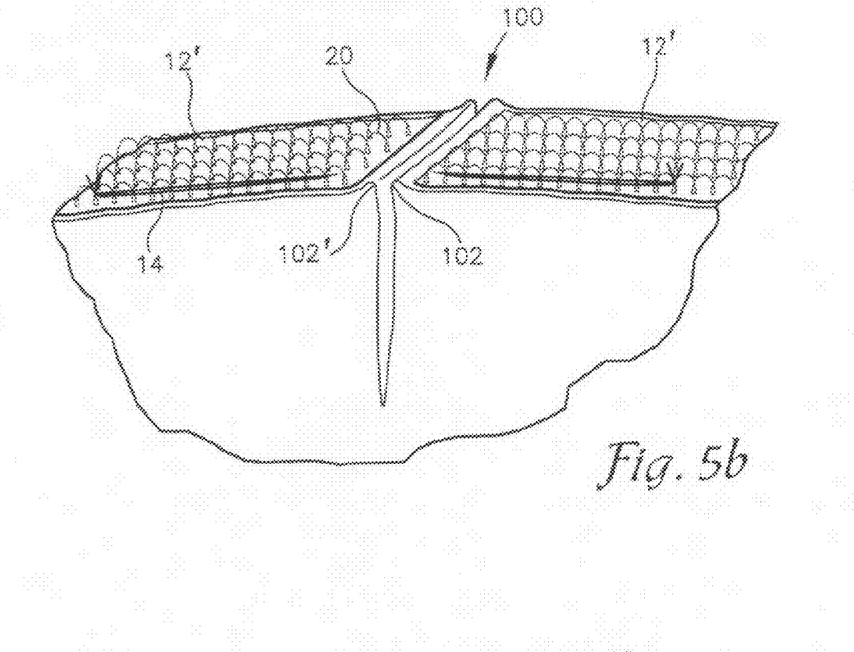
FIG. 5b is a cross-section illustration of the wound edges being everted using the system.

A particular advantage of the present method and device is that it permits eversion of inverted wound edges 102' before drawing those edges together. With reference to FIG. 5a, many wounds involve at least one inverted wound edge 102'. Those skilled in the art will recognize that inverting suture patterns are often associated with delayed healing. Thus, appositional or everting sutures are preferred for many tissue closure as they provide the best anatomical approximation of the disrupted tissue planes. More recently, there has been a recognition of a benefit for a slight eversion on skin closures, because the scar has a tendency to flatten rather than widen. Therefore, as depicted in FIG. 5b, in one or more embodiments, the thread 14 can be secured to an anchoring member 20 proximate to an inverted wound edge 102', and then drawn away from and secured to an anchoring member 20 distal from the wound edge 102' (on that same side of the wound 100) to evert the edge 102'. This procedure can be repeated as necessary or desired on all edges 102 of the wound 100 before subsequently drawing the edges 102 together. Alternatively, if it is noticed that an edge of the wound 102 has become inverted during the process of lacing together the substrate pieces 12', this same procedure can be used to evert the wound edge 102' from the closed wound 100'.

A further advantage of the system and method is that if the approximation of the tissue during wound closure is not satisfactory, the thread 14 can simply be cut and removed from the anchoring members 20 and the wound closure can be re-done without creating any additional trauma to the subject. This is particularly advantageous in cosmetic incision closure where scars and scarring should be minimized as much as possible. It is not practical to remove and re-suture using traditional suturing or staple gun techniques because of the added trauma caused to the subject and the tissue during such a process. Likewise, most wound closure adhesives simply cannot be practically removed from the wound once used to close the tissue. A further advantage is that because this technique is sutureless, removable, and "re-doable," it can be used by unskilled persons to close a wound in emergency or short-term situations and mediate further trauma and/or blood loss until the subject can be attended to by a medical practitioner. As noted above, the medical practitioner can then remove the threads and re-close the wound, if necessary. This would be particularly advantageous for home first aid kits, hikers, as well as for soldiers on the battle field.

The atraumatic wound closure system also reduces or even completely eliminates the need for sedation and/or anesthesia, which can be an important factor in treating pediatric and/or veterinary patients. Moreover, the wound itself remains visible for evaluation of infection allowing for better local wound care and healing. The lack of sutures, staples, or other foreign bodies piercing the skin also reduces the risk of infection as well as promotes blood flow (and accordingly healing). In addition, if the wound does become infected, the present method of wound closure allows for easier egress of purulent fluid and material from the wound.

A kit for the atraumatic closure of wound tissue is also provided herein. The kit comprises one or more substrates as described above, optionally thread for lacing together the substrates, and instructions for using the substrate and thread to close a wound. Template material can also be included in the kit, along with scissors or other devices for cutting the substrate to fit the wound shape. Additional conventional first-aid components, such as disinfectant, antibiotic ointment, alcohol, betadine, chlorhexidine, and the like can also be included in the kit.

It will be appreciated that the wound closure system described herein may be used, in one or more embodiments, in addition to traditional wound closure techniques to further stabilize and support the tissue adjacent (i.e., next to) the wound. The system could be used before traditional wound closure to facilitate pushing the disrupted tissue planes together for traditional suturing, etc. Alternatively, the system could be applied after traditional wound closure to relieve pressure or tension on the wound edges due to the conventional sutures, staples, etc. used to close the wound. In other embodiments, the system is used entirely in lieu of conventional wound closure techniques. Thus, the tissue of the subject is not pierced (by suture, staple, etc.) before, during, or after the process of reapproximating the wound edges using the inventive system.

Figures 7A, 7B:
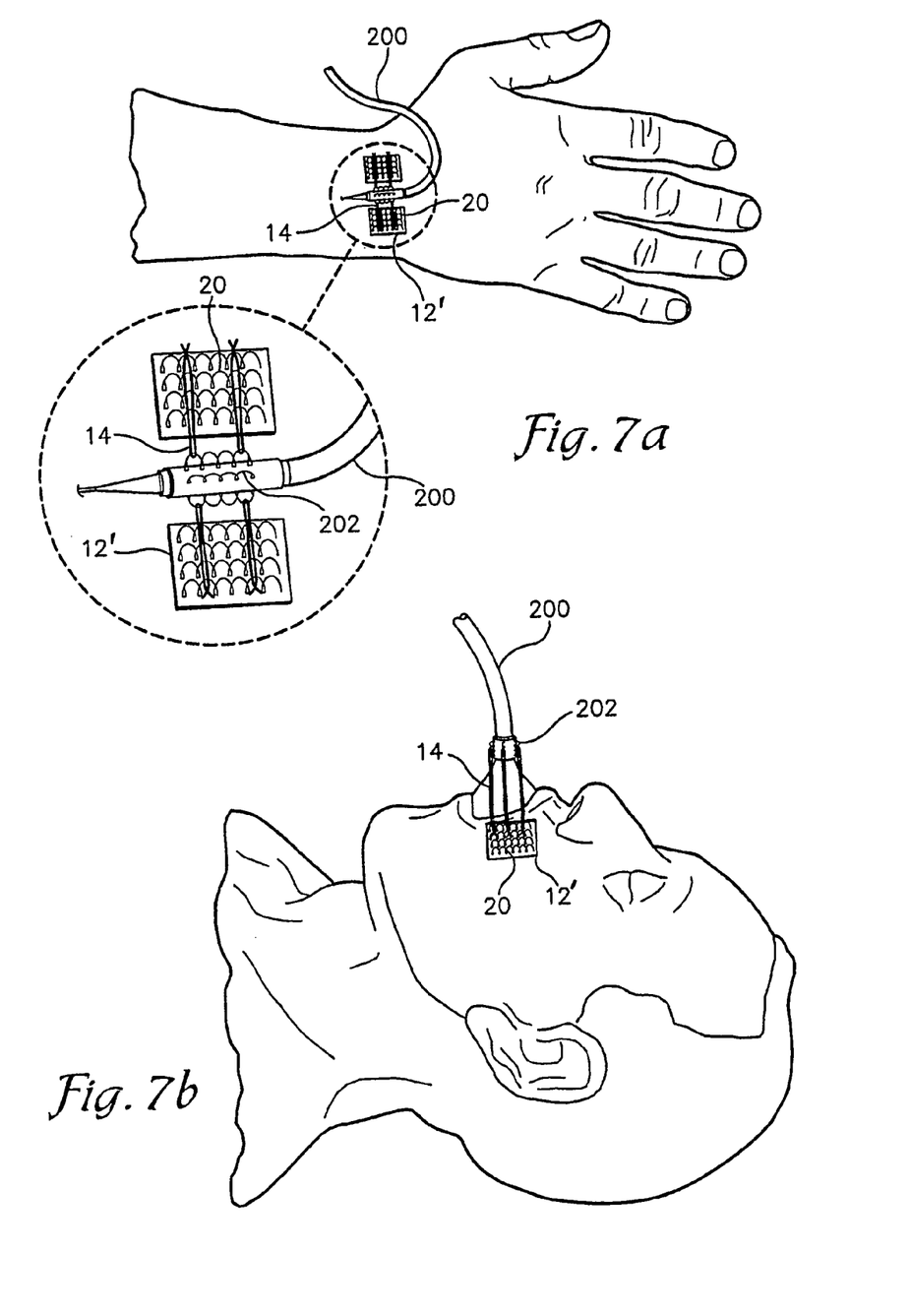
FIG. 7a is a perspective view an IV tube inserted in a subject's arm that is secured to the patient using the system.
FIG. 7b is a side elevational view of a patient that has been intubated, wherein the tube is secured to the patient using the system.

It will also be appreciated that, instead of securing wound edges to close a wound, the present system could also be used to secure medical devices, packing, dressings, and the like to a patient without piercing the subject's tissue. For example, in one or more embodiments, the invention is also concerned with atraumatic securement of a medical device to a patient. The method comprises inserting a medical device 200 into the patient and securing the device to the patient's tissue using the wound care system 10. In particular, one or more pieces of the substrate 12' are adhered to tissue on either side of the device 200, as depicted in FIGS. 7a and b. The device 200 is then secured to the substrate 12' using the thread 14, which is secured between any suitable attachment points 202 on the device 200 and the anchoring members 20. For example, the thread 14 can be secured to a first anchoring member 20 on one side of the device 200 (e.g., by tying it off on one of the anchoring members 20) and then passed to an attachment point 202 on the device before being passed to the other side of the device 200 where it is secured to/threaded through a second anchoring member 20 on the other side of the device 200 such that tension is created on both sides of the device 200 to hold it in place. The back and forth process can be repeated using various anchoring members 20 on either side of the device 200 until sufficiently secured in place to avoid being dislodged. It will be appreciated that the device 200 can be secured using a single continuous thread 14, or multiple threads 14 that are tied off or fastened at various points in the threading process. It will also be appreciated that the thread 14 can be passed through a single anchoring member 20 multiple times during the lacing process, which unlike a conventional suture, allows that single point to be tethered and stabilized from multiple directions, reducing any single directional force/tension on the tissue at that spot. Those skilled in the art will also appreciate that one advantage of the invention is that there is little to no additional localized trauma to the patient to secure the device, which can be easily removed by cutting or removing the thread 14. The method would be suitable for securing various devices to a patient, include tracheal tubes, nasogastric tubes, ventilators, drains, catheters, IVs, central lines, arterial lines, and the like.

Figure 8A:
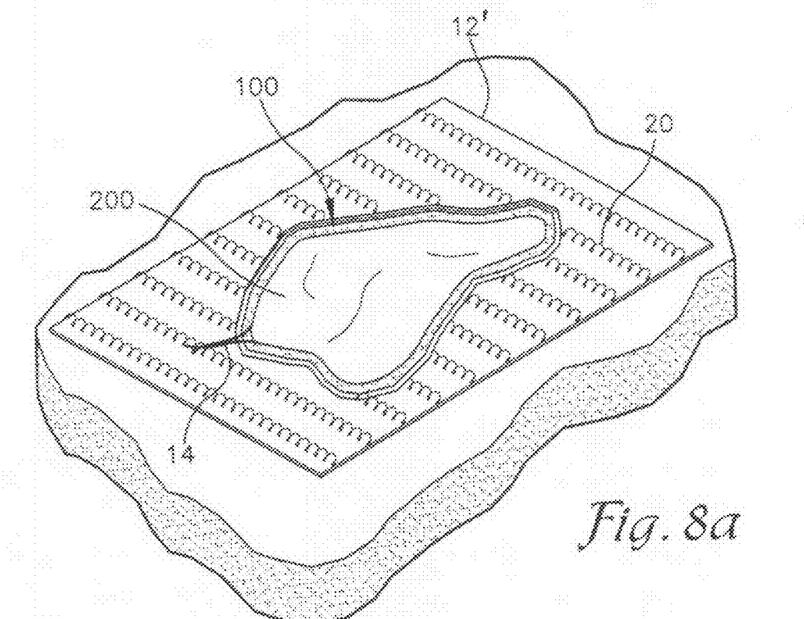
FIG. 8a illustrates an open wound filled with sterile packing material, with a portion of the packing external to the wound secured to the wound care substrate.
Figure 8B:
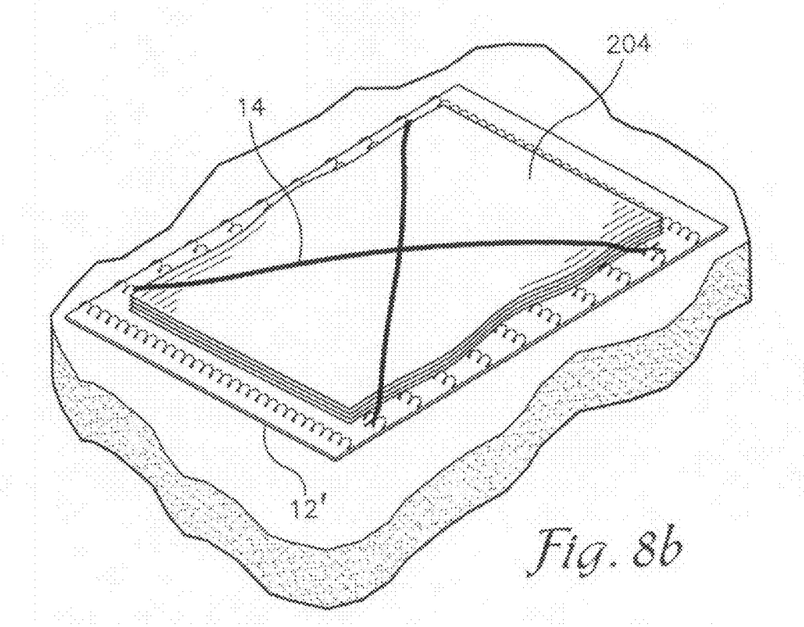
FIG. 8b illustrates a dressing secured over a wound using the system.
Figure 9:
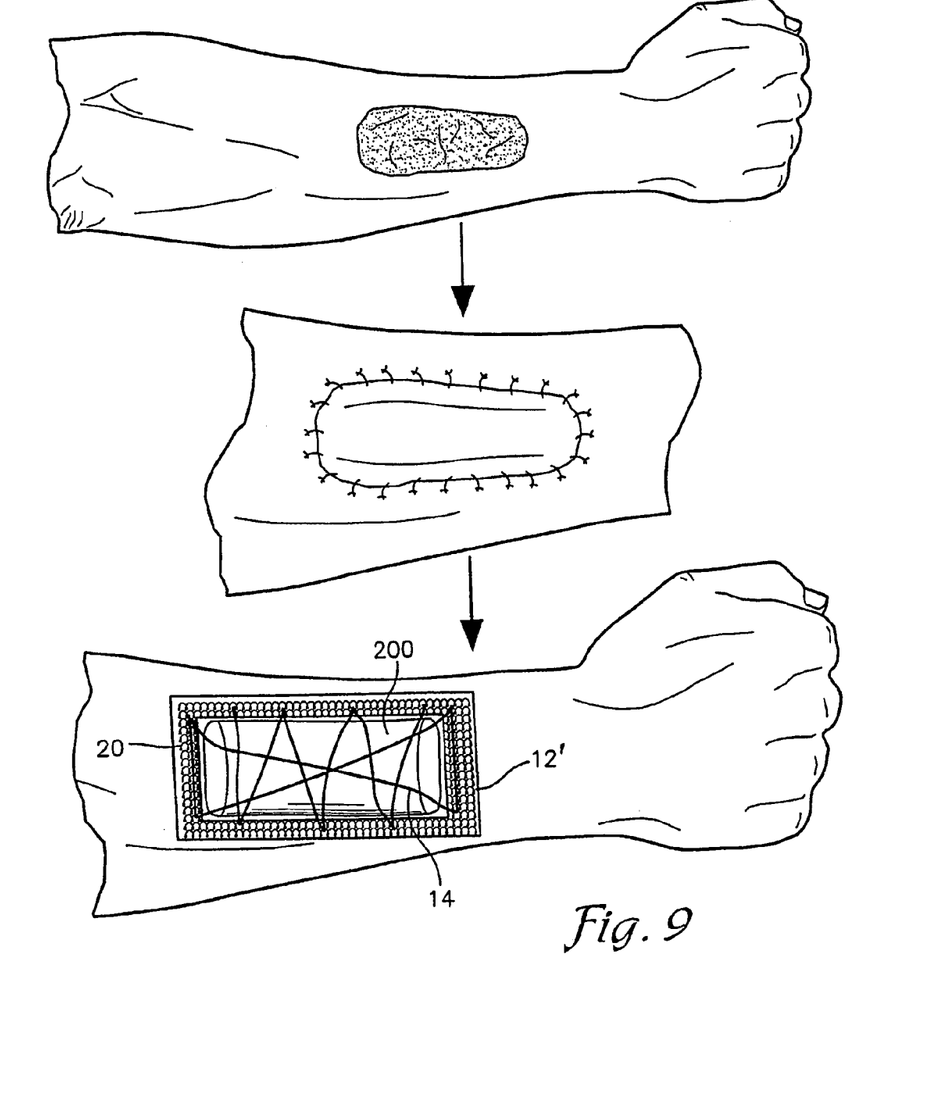
FIG. 9 illustrates a process of grafting a burn wound and then securing a bolster dressing over the wound using the system.
Figure 10:
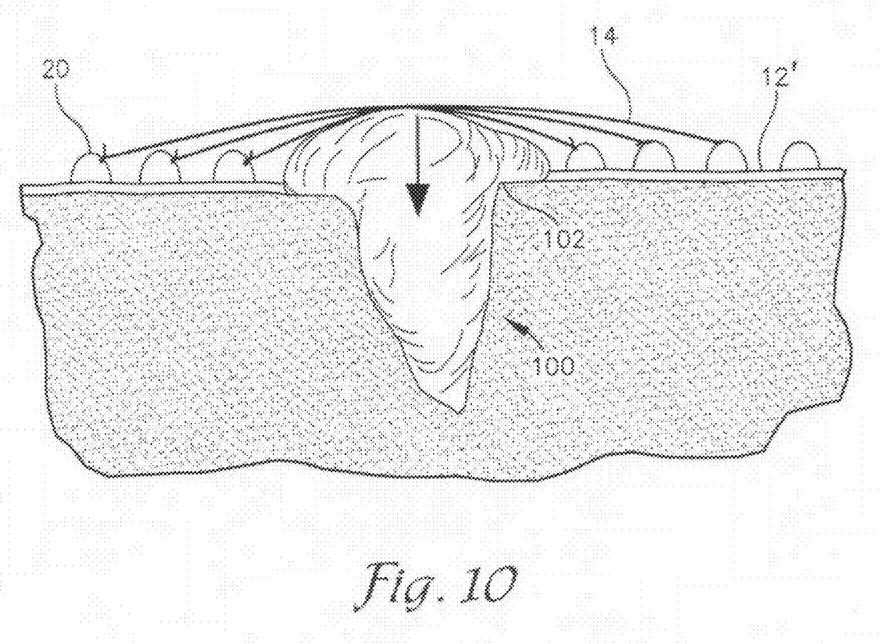
FIG. 10 illustrates use of system to secure a pressure dressing over a wound.

In one or more embodiments, the system 10 can be used to secure wound packing and dressings. This is particularly advantageous for packings that need to be removed and replaced daily or multiple times per day, and avoids the repeat trauma to the patient that is encountered by repeated application and removal of dressing tape and other similar coverings. One or more pieces of the substrate 12' can be adhered to tissue adjacent (i.e., next to) the wound 100 which has been packed with suitable packing material (e.g., sterile gauze, etc.) 200. Typically, the "tail" of the packing material 200 remains outside of the wound to facilitate removal of the packing. In the present system 10, the tail can advantageously be secured to the substrate 12' using the thread 14. A dressing 204 is then placed over the packed wound, and the system 10 is used to secure the dressing over the wound using the thread 14 and the anchoring members 20, as depicted in FIGS. 8a and 8b. The wound care system 10 can also be used to secure bolster dressings or other like dressings in a similar manner, as depicted in FIG. 9, which are often used with burn wounds and skin grafts, and are typically sutured to the skin, again creating additional trauma on the patient. In one or more embodiments, the system 10 can also be used as part of a pressure dressing to stop bleeding and temporarily stabilize the patient until definitive care can be obtained, as depicted in FIG. 10. Thus, the system is suitable for use with various wound dressings, such as cotton 4×4, and the like. It will be appreciated that in each of the foregoing wound care methods, the system 10 has an additional benefit of significance to patient care. After the applicable dressing, packing, or the like is removed from the patient at the appropriate stage of healing (i.e., by cutting or removing the thread 14 to permit removal of the care device), the substrate can remain in place adjacent (i.e., next to) the wound. Using thread, the system can then be used to subsequently close the wound for permanent healing. Again, the system provides a significant advantage in that the tissue adjacent (i.e., next to) the wound does not have to undergo additional trauma from the application and/or removal of tape, adhesives, and the like, to remove the dressings, packing, etc., and does not have to be pierced or punctured using staples or suture to subsequently close the wound. This provides an important advancement in the state of the art of wound care and closure.

The present substrate also finds usefulness as a novelty item. For example, the substrate described above can also be used to repair or close ripped seams or other tears in stuffed animals. It will be appreciated that the substrate 12 will comprise an adhesive layer suitable for bonding to a fabric and/or synthetic "fur" surface. Thus, considerations as noted above with respect to biocompatibility will not be as much of a factor in such an embodiment; however, the method of use remains substantially the same as that described above for wound closure. The substrate could be provided, for instance, as part of a teddy bear repair kit. The thread would be provided generally without a needle, such that the kit would be suitable for use by children to repair their stuffed animals. The kit would also be suitable for use as part of a children's doctor set for pretend suturing of "patients."

Additional advantages of the various embodiments of the disclosure will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

In addition, while the drawings illustrate, and the specification describes, certain preferred embodiments, it is to be understood that such disclosure is by way of example only. Embodiments are described herein with reference to illustrations of idealized embodiments of the present invention. As such, variations from the shapes of the illustrations as a result, for example, of manufacturing techniques and/or tolerances, are to be expected. There is no intent to limit the principles of the present embodiments to the particular disclosed embodiments. For example, in the drawings, the size and relative sizes of components may be exaggerated for clarity. In addition, embodiments should not be construed as limited to the particular shapes of regions illustrated herein but are to include deviations in shapes that result, for example, from manufacturing.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination. The term "adjacent" means adjoining, abutting (touching) so as to have a common interface/surface or border. In the case of layers, a layer is considered to be adjacent when it shares a common interface (i.e., is in face-to-face contact) with the adjacent structure. With respect to wound tissue, tissue that is adjacent to the wound refers to tissue proximate to the wound but not involving the wound edges (i.e., tissue spaced slightly from the wound edges themselves).

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

What is claimed:

1. A method for the atraumatic closure of a tissue wound of a subject, said wound having wound edges, said method comprising:
    providing an article and a thread, said article comprising:
        a substrate having opposing first and second major surfaces;
        a plurality of raised anchoring members disposed across said first major surface; and
        an optional adhesive adjacent said second major surface;
    adhering said article substrate to said tissue adjacent said wound edges on a first side of said wound and on a second side of said wound opposite said first side; and
    reapproximating said wound edges by:
        securing said thread to a first anchoring member on said first side of said wound,
        passing said thread to said second side of said wound opposite said first side and securing said thread to a second anchoring member, and
        repeating said securing and said passing along the wound edges, said thread being under tension and pulling said tissue from said first side of said wound towards said tissue on said second side of said wound thereby closing said wound.

2. The method of claim 1, wherein said substrate is a continuous, flexible web, comprising a pair of laterally spaced longitudinal side edges and a pair of laterally spaced transverse ends.

3. The method of claim 1, wherein said substrate is severable.

4. The method of claim 1, wherein said substrate comprises a woven or nonwoven web of cotton, silk, hemp, flax, rayon, polyester, acrylic, acrylate, polyolefin, nylon, polyurethane, polyethylene, polyester, wire, and/or embedded wire clothe.

5. The method of claim 1, wherein said anchoring members are selected from the group consisting of loops, half-loops, eyelets, mesh, hooks, pegs, prongs, nubs, generally upright strands of fiber, prone strands of fiber, pleats, and combinations thereof.

6. The method of claim 1, wherein said anchoring members are disposed substantially uniformly across said first major surface.

7. The method of claim 1, wherein said anchoring members project away from said first major surface, and have respective heights, as measured from said first major surface, of from about 1 mm to about 20 mm.

8. The method of claim 1, wherein said adhesive is in the form of a layer adjacent said second major surface, and is selected from the group consisting of pressure sensitive adhesives, heat-activated adhesives, and radiation-activated adhesives.

9. The method of claim 1, wherein said adhering comprises:
    applying adhesive to said tissue adjacent said wound edges on a first side of said wound and on a second side of said wound opposite said first side; and
    mounting said article substrate to said adhesive with said second major surface being in contact with said adhesive.

10. The method of claim 1, further comprising:
determining the shape of the edges of said wound;
severing said substrate into one or more pieces to conform to said shape, prior to adhering said pieces to tissue adjacent said wound edges.

11. The method of claim 1, wherein the tissue of said subject is not pierced during said reapproximating.

12. The method of claim 1, wherein at least one of said wound edges is inverted, further comprising:
securing a thread to an anchoring member proximate to said inverted wound edge;
drawing said thread away from said wound edge; and
securing said thread to an anchoring member distal from said wound edge thereby lifting said inverted wound edge to yield an everted wound edge.

13. A kit for the atraumatic closure of a wound, said kit comprising:
an article comprising:
a substrate having opposing first and second major surfaces;
a plurality of raised anchoring members disposed across said first major surface; and
an optional adhesive adjacent said second major surface;
optionally a thread; and
instructions for using said article and a thread to close a wound.

14. The kit of claim 13, wherein said thread comprises a substantially rigid end portion, or wherein said kit further comprises a needle configured to guide said thread.

15. The kit of claim 13, wherein said article does not comprise adhesive adjacent said second major surface, said kit further comprising an adhesive for mounting said article to tissue or fabric.

16. The kit of claim 13, further comprising:
a template for determining the shape of said wound;
a device for cutting said article; and
a first-aid component selected from the group consisting of disinfectant, isopropyl alcohol, antibiotic ointment, betadine, chlorhexidine, and combinations thereof.

17. A method for the atraumatic care of a wound of a subject, said wound having wound edges, said method comprising:
providing an article and a thread, said article comprising:
a substrate having opposing first and second major surfaces;
a plurality of raised anchoring members disposed across said first major surface; and
an optional adhesive adjacent said second major surface;
adhering said article substrate to said tissue adjacent said wound edges on a first side of said wound and on a second side of said wound opposite said first side;
covering said wound with a dressing; and
securing said dressing to said wound by:
securing said thread to a first anchoring member on said first side of said wound, passing said thread over said dressing to said second side of said wound opposite said first side and securing said thread to a second anchoring member, and
repeating said securing and said passing over said dressing along the wound edges, said thread being under tension and pressing said dressing towards said wound, thereby securing said dressing to said wound.

18. The method of claim 17, wherein said wound is filled with sterile packing prior to covering said wound with dressing, said method further comprising:
removing said dressing by cutting said thread;
removing said packing from said wound;
re-packing said wound with a sterile packing;
covering said wound with a dressing; and
securing said dressing to said wound by:
securing a thread to a first anchoring member on said first side of said wound,
passing said thread over said dressing to said second side of said wound opposite said first side and securing said thread to a second anchoring member, and
repeating said securing and said passing over said dressing along the wound edges, said thread being under tension and pressing said dressing towards said wound, thereby securing said dressing to said wound.

19. A method for the atraumatic securement of a medical device to a patient's tissue, said method comprising:
providing an article and a thread, said article comprising:
a substrate having opposing first and second major surfaces;
a plurality of raised anchoring members disposed across said first major surface; and
an optional adhesive adjacent said second major surface;
inserting a medical device into said patient;
adhering said article substrate to said tissue adjacent where said device is inserted into said patient on a first side of said device and on a second side of said device opposite said first side;
securing a thread to a first anchoring member on said first side of said device and to said device; and
securing a thread to a second anchoring member on said second side of said device and to said device, wherein said thread on each side of said device is under tension to stabilize and prevent dislodgement of said device from said patient.

20. The method of claim 19, wherein said device is selected from the group consisting of tracheal tubes, nasogastric tubes, ventilators, drains, catheters, IVs, central lines, arterial lines, and combinations thereof.

* * * * *